(12) United States Patent
Caulfield et al.

(10) Patent No.: US 8,362,416 B2
(45) Date of Patent: *Jan. 29, 2013

(54) METHODS FOR DETECTING CATECHOLAMINES BY MASS SPECTROMETRY

(75) Inventors: Michael P. Caulfield, San Clemente, CA (US); Gloria Kwangja Lee, Ladera Ranch, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 10 days.

This patent is subject to a terminal disclaimer.

(21) Appl. No.: 13/084,446

(22) Filed: Apr. 11, 2011

(65) Prior Publication Data

US 2011/0240843 A1    Oct. 6, 2011

Related U.S. Application Data

(63) Continuation of application No. 12/336,502, filed on Dec. 16, 2008, now Pat. No. 7,952,068.

(51) Int. Cl.
*H01J 49/00* (2006.01)

(52) U.S. Cl. ............................................ 250/282; 435/6

(58) Field of Classification Search .................. 250/282, 250/281; 435/6; 436/518, 536
See application file for complete search history.

(56) References Cited

U.S. PATENT DOCUMENTS

| | | | |
|---|---|---|---|
| 5,722,874 A | 3/1998 | Horton et al. | |
| 5,795,469 A | 8/1998 | Quinn et al. | |
| 5,919,368 A | 7/1999 | Quinn et al. | |
| 5,968,367 A | 10/1999 | Quinn et al. | |
| 6,107,623 A | 8/2000 | Bateman et al. | |
| 6,124,137 A | 9/2000 | Hutchens et al. | |
| 6,204,500 B1 | 3/2001 | Whitehouse et al. | |
| 6,268,144 B1 | 7/2001 | Koster | |
| 6,623,928 B2 | 9/2003 | Van Ness et al. | |
| 7,052,846 B2 * | 5/2006 | Van Ness et al. | 435/6.12 |
| 7,456,027 B2 * | 11/2008 | Wang et al. | 436/503 |
| 7,952,068 B2 * | 5/2011 | Caulfield et al. | 250/282 |
| 2006/0183238 A1 | 8/2006 | Nimkar et al. | |

OTHER PUBLICATIONS

Bartolucci, et al., Liquid chromatography tandem mass spectrometric quantitation of sulfamethazine and its metabolites: direct analysis of swine urine by triple quadrupole and by ion trap mass spectrometry, Rapid Commun. Mass Spectrom. 14.967-73 (2000).

Carrera, V., et al., A simple and rapid HPLC-MS method for the simultaneous determination of epinephrine, norepinephrine, dopamine and 5-hydroxytryptamine: Application to the secretion of bovine chromaffin cell cultures, J Chromatog. B, 847:88-94 (2007).

Chan, E., et al., High-performance liquid chromatographic assay for catecholamines and metanephrines using fluorimetric detection with pre-column 9-fluorenylmethyloxycarbonyl chloride derivatization, J Chromatog. B, 749:179-189 (2000).

Chan, E., et al., High-performance liquid chromatography/atmospheric pressure chemical ionization mass spectrometric method for the analysis of catecholamines and metanephrines in human urine, Rapid Commun. Mass Spectrom., 14:1959-1964 (2000).

(Continued)

*Primary Examiner* — Kiet T Nguyen
(74) *Attorney, Agent, or Firm* — Foley & Lardner LLP

(57) ABSTRACT

Provided are methods for determining the amount of one or more of one or more of epinephrine (E), norepinephrine (NE), and dopamine (D) in a sample using mass spectrometry. The methods generally involve ionizing one or more of E, NE, and D in a sample and detecting and quantifying the amount of the ion to determine the amount of one or more of E, NE, and D in the sample.

15 Claims, 9 Drawing Sheets

OTHER PUBLICATIONS

Eriksson, B., et al., Determination of catecholamines in urine by liquid chromatography and electrochemical detection after on-line sample purification on immobilized boronic acid, J Chromatog., 593:185-190 (1992).

Gu, Q., et al., Analysis of catecholamines and their metabolites in adrenal gland by liquid chromatography tandem mass spectrometry, Analytica Chimica Acta, 609:192-200 (2008).

Heki, N., et al., Mass fragmentography—An improved method for the simultaneous analysis of norepinephrine, epinephrine and dopamine ant the pictogram level by mass fragmetography, Nippon Naibunpi Gakkai Zasshi, 53:785-96 (1977). (The article is in Japanese but an English language abstract has been provided).

Kushnir, M., et al., Analysis of Catecholamines in Urine by Positive-Ion Electrospray Tandem Mass Spectrometry, Clin. Chem., 48:323-31 (2002).

Lemos-Amado, F., et al., Electrospray tandem mass spectrometry of aminochromes, Rapid Commun. Mass Spectrom., 15:2466-71 (2001).

Merchant and Weinberger, Recent advancements in surface-enhancer laser desorption/ionization of flight-mass spectrometry, Electrophoresis, 21: 1164-67 (2000).

Polson et al.,Optimization of protein precipitation based upon effectiveness of protein removal and ionization effect in liquid chromatography 13 tandem mass spectrometry, Journal of Chromatography B, 785:263-275 (2003).

Robb et al., Atmospheric Pressure Photoionization: An Ionization Method for Liquid Chromatography-Mass Spectrometry, Anal. Chem., 72(15): 3653-3659 (2000).

Smythe, G., et al., Biochemical Diagnosis of Pheochromocytoma by Simultaneous Measurement of Urinary Excretion of Epinephrine and Norepinephrine, Clin. Chem., 38:486-92 (1992).

Soga, T., and Inoue, Y., Determination of catecholamines in urine and plasma by on-line sample pretreatment using an internal surface boronic acid gel, J Chromatog., 620:175-81 (1993).

Törnkvist, A., et al., Analysis of catecholamines and related substances using porous graphitic carbon as separation media in liquid chromatography-tandem mass spectrometry, J Chromatog. B, 801:323-329 (2004).

US Notice of Allowance dated Mar. 3, 2011 in U.S. Appl. No. 12/336,502.

Wright et al., Proteinchip® surface enhanced laser desorpotion/ionization (SELDI) mass spectrometry: a novel protein biochip technology for detection of prostate cancer biomarkers in complex protein mixtures, Prostate Cancer and Prostatic Diseases, 2: 264-76 (1999).

Zimmer et al., Comparison of turbulent-flow chromatography with automated solid-phase extraction in 96-well plates and liquid-liquid extraction used as plasma sample preparation techniques for liquid chromatography-tandem mass spectrometry, J Chromatogr A, 854: 23-35 (1999).

* cited by examiner

METHODS FOR DETECTING CATECHOLAMINES BY MASS SPECTROMETRY

CROSS-REFERENCE TO RELATED PATENT APPLICATION

This application is a continuation of U.S. application Ser. No. 12/336,502 tiled Dec. 16, 2008, which is incorporated herein by reference in its entirety.

FIELD OF THE INVENTION

The invention relates to the detection of catecholamines. In a particular aspect, the invention relates to methods for detecting epinephrine, norepinephrine, and dopamine by mass spectrometry.

BACKGROUND OF THE INVENTION

The following description of the background of the invention is provided simply as an aid in understanding the invention and is not admitted to describe or constitute prior art to the invention.

In the central nervous system, neurons produce dopamine (D) and norepinephrine (NE) which act as neurotransmitters. The adrenal medulla produces both epinephrine (E) and NE while NE is liberated by postganglionic sympathetic nerves. Conversion of NE to E occurs mainly in the adrenal medulla. When catecholamines are released from sympathetic tissue, other than the adrenal medulla, the primary means of physiologic inactivation is the return of unaltered catecholamines by an active transport mechanism. The residual hormone may then be metabolized or excreted unchanged by the kidney.

Two enzymes are important for catecholamine metabolism; monoamine oxidase (MAO), which is responsible for oxidative deamination and catechol-O-methyltransferase (COMT), which is responsible of O-methylation. COMT is principally responsible for inactivating circulating catecholamines, whereas MAO is thought to play a role in disposing of excess catecholamine stores. The major end product for metabolism of E and NE is 3-methoxy-4-hydroxymandelic acid (VMA). The other urinary metabolites of the catecholamines are metanephrine and normetanephrine.

Tyrosine is the amino acid precursor of the catecholamines. The major catecholamine biosynthetic pathways are shown below.

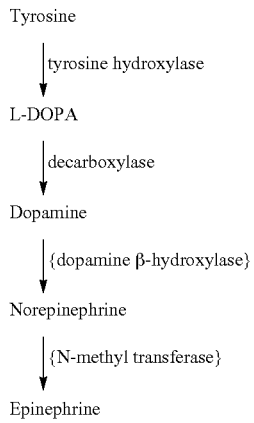

Methods for purifying catecholamines in a sample utilizing boronic acid have been reported. See, e.g., Soga, T., et al., *J. Chromatog.* 1993, 620:175-81; and Eriksson, B., et al., *J. Chromatog.* 1992, 593:185-190. Various mass spectrometric techniques for measuring catecholamines in a sample have been reported. See, e.g., Smythe, G., et al., *Clin. Chem.*, 1992, 38:486-92; Heki, N., et al., *Nippon Naibunpi Gakkai Zasshi* 1977, 53:785-96; Lemos-Amado, F., et al., *Rapid Commun. Mass Spectrom.* 2001, 15:2466-71; Chan, E., et al., *J. Chromatog. B* 2000, 749:179-189; Nimkar, S., et al., U.S. patent application Ser. No. 11/350,147 (filed Feb. 8, 2006); Chan, F., et al., *Rapid Commun. Mass Spectrom.* 2000, 14:1959-64; Tornkvist, A., et al., *J Chromatog, B* 2004, 801:323-9; Gu, Q., et al., *Analytica Chimica Acta* 2008, 609:192-200; Kushnir, M., et al., *Clin. Chem.* 2002, 48:323-31; and Carrera, V., et al., *J Chromatog, B* 2007, 847:88-94.

SUMMARY OF THE INVENTION

The present invention provides methods for detecting the amount of one or more of epinephrine (E), norepinephrine (NE), and dopamine (D) in the sample by mass spectrometry, including tandem mass spectrometry. In methods where multiple analytes are detected, the multiple analytes are detected in the same sample injection.

In one aspect, methods are presented for determining in a sample the amount of one or more analytes selected from the group consisting of epinephrine, norepinephrine, and dopamine. In some embodiments of this aspect, the methods include subjecting the sample to ionization under conditions suitable to produce one or more ions detectable by mass spectrometry; determining the amount of the one or more ions by tandem mass spectrometry; and using the amount of the one or more ions to determine the amount of the one or more analytes in the sample. In these embodiments, if one of the one or more analytes is epinephrine, the ionizing comprises generating ions with a mass to charge ratio of 166.1±0.50; if one of the one or more analytes is norepinephrine, the ionizing comprises generating ions with a mass to charge ratio of 151.9±0.50; and if one of the one or more analytes is dopamine, the ionizing comprises generating ions with a mass to charge ratio of 136.9±0.50. In some embodiments, the sample is urine. In some embodiments, the analytes are purified by immobilized boronic acid extraction prior to ionization; preferably the immobilized boronic acid is boronic acid immobilized in a gel.

In some embodiments, if one of the one or more analytes is epinephrine, the ionization comprises generating ions with a mass to charge ratio of 166.1±0.50 and ions with a mass to charge ratio of 107.0±0.50; if one of the one or more analytes is norepinephrine, the ionization comprises generating ions with a mass to charge ratio of 151.9±0.50 and ions with a mass to charge ratio of 107.0±0.50; and if one of the one or more analytes is dopamine, the ionization comprises generating ions with a mass to charge ratio of 136.9±0.50 and ions with a mass to charge ratio of 91.0±0.50.

In some embodiments, if one of the one or more analytes is epinephrine, the ionization comprises generating parent ions with a mass to charge ratio of 166.1±0.50 and fragment ions with a mass to charge ratio of 107.0±0.50; if one of the one or more analytes is norepinephrine, the ionization comprises generating parent ions with a mass to charge ratio of 151.9±0.50 and fragment ions with a mass to charge ratio of 107.0±0.50; and if one of the one or more analytes is dopamine, the ionization comprises generating parent ions with a mass to charge ratio of 136.9±0.50 and fragment ions with a mass to charge ratio of 91.0±0.50.

In some embodiments, the amounts of two or more of the analytes from the group consisting of epinephrine, norepinephrine, and dopamine are determined in the same sample injection. In some embodiments, the amounts of epinephrine, norepinephrine, and dopamine are determined in the same sample injection.

In other embodiments of this aspect, methods are presented which include subjecting the sample following purification by immobilized boronic acid extraction to ionization under conditions suitable to produce one or more ions detectable by tandem mass spectrometry from the one or more analytes; determining the amount of one or more ions by tandem mass spectrometry; and using the amount of the one or more ions to determine the amount of the one or more analytes in the sample. In some of these embodiments, the sample comprises urine. Preferably, the immobilized boronic acid is boronic acid immobilized in a gel.

In some embodiments, if one of the one or more analytes is epinephrine, the ionization comprises generating ions with a mass to charge ratio of $166.1\pm0.50$; if one of the one or more analytes is norepinephrine, the ionizing comprises generating ions with a mass to charge ratio of $151.9\pm0.50$; and if one of the one or more analytes is dopamine, the ionization comprises generating ions with a mass to charge ratio of $136.9\pm0.50$.

In some embodiments, if one of the one or more analytes is epinephrine, the ionization comprises generating ions with a mass to charge ratio of $166.1\pm0.50$ and ions with a mass to charge ratio of $107.0\pm0.50$; if one of the one or more analytes is norepinephrine, the ionization comprises generating ions with a mass to charge ratio of $151.9\pm0.50$ and ions with a mass to charge ratio of $107.0\pm0.50$; and if one of the one or more analytes is dopamine, the ionization comprises generating ions with a mass to charge ratio of $136.9\pm0.50$ and ions with a mass to charge ratio of $91.0\pm0.50$.

In some embodiments, if one of the one or more analytes is epinephrine, the ionization comprises generating parent ions with a mass to charge ratio of $166.1\pm0.50$ and fragment ions with a mass to charge ratio of $107.0\pm0.50$; if one of the one or more analytes is norepinephrine, the ionization comprises generating parent ions with a mass to charge ratio of $151.9\pm0.50$ and fragment ions with a mass to charge ratio of $107.0\pm0.50$; and if one of the one or more analytes is dopamine, the ionization comprises generating parent ions with a mass to charge ratio of $136.9\pm0.50$ and fragment ions with a mass to charge ratio of $91.0\pm0.50$.

In some embodiments, the amounts of two or more of the analytes from the group consisting of epinephrine, norepinephrine, and dopamine are determined in the same sample injection. In some embodiments, the amounts of epinephrine, norepinephrine, and dopamine are determined in the same sample injection.

In a second aspect, methods are presented for determining the amount of one or more analytes selected from the group consisting of epinephrine and dopamine in the same urine sample. These methods include subjecting the sample to ionization under conditions suitable to produce one or more ions detectable by mass spectrometry; determining the amount of one or more ions by mass spectrometry; and using the amount of the one or more ions to determine the amount of the one or more analytes in the sample. In these embodiments, if one of the one or more analytes is epinephrine, the ionization comprises generating ions with a mass to charge ratio of $166.1\pm0.50$; and if one of the one or more analytes is dopamine, the ionization comprises generating ions with a mass to charge ratio of $136.9\pm0.50$. In some embodiments, the mass spectrometry is tandem mass spectrometry.

In some embodiments, if one of the one or more analytes is epinephrine, the ionization comprises generating ions with a mass to charge ratio of $166.1\pm0.50$ and ions with a mass to charge ratio of $107.0\pm0.50$; and if one of the one or more analytes is dopamine, the ionization comprises generating ions with a mass to charge ratio of $136.9\pm0.50$ and ions with a mass to charge ratio of $91.0\pm0.50$.

In some embodiments, if one of the one or more analytes is epinephrine, the ionization comprises generating parent ions with a mass to charge ratio of $166.1\pm0.50$ and fragment ions with a mass to charge ratio of $107.0\pm0.50$; and if one of the one or more analytes is dopamine, the ionization comprises generating parent ions with a mass to charge ratio of $136.9\pm0.50$ and fragment ions with a mass to charge ratio of $91.0\pm0.50$.

In some embodiments, the amounts of epinephrine and dopamine are determined in the same sample injection.

In some embodiments, methods further comprise determining the amount of norepinephrine in the same urine sample. In these embodiments, the step of subjecting the sample to ionization under conditions suitable to produce one or more ions detectable by mass spectrometry further comprises generating ions with a mass to charge ratio of $151.9\pm0.50$, and the amount of one or more ions determined by mass spectrometry is used to determine the amount of norepinephrine in the sample.

In some embodiments, ionization comprises generating ions with a mass to charge ratio of $151.9\pm0.50$ and ions with a mass to charge ratio of $107.0\pm0.50$.

In some embodiments, ionization comprises generating parent ions with a mass to charge ratio of $151.9\pm0.50$ and fragment ions with a mass to charge ratio of $107.0\pm0.50$.

In some embodiments, the amounts of epinephrine, norepinephrine, and dopamine are determined in the same sample injection.

In some embodiments, one or more analytes are purified by immobilized boronic acid extraction from the sample. In preferred embodiments immobilized boronic acid is boronic acid immobilized in a gel.

In a third aspect, methods are presented for determining the amount of epinephrine, norepinephrine, and dopamine in a urine sample from the same sample injection. These methods include subjecting the sample ion ionization under conditions suitable to produce one or more ions detectable by mass spectrometry from each of the analytes; determining the amount of one or more ions by mass spectrometry; and using the amount of the one or more ions to determine the amount of epinephrine, norepinephrine, and dopamine in the sample. In these methods, ionization comprises generating ions from the group consisting of ions with a mass to charge ratio of $166.1\pm0.50$, $151.9\pm0.50$, and $136.9\pm0.50$. In some embodiments, the mass spectrometry is tandem mass spectrometry. In some embodiments, the sample has been purified by immobilized boronic acid extraction prior to ionization. In preferred embodiments, immobilized boronic acid is boronic acid immobilized in a gel.

The features of the embodiments listed above may be combined without limitation for use in methods of the present invention.

Methods of the present invention may involve the combination of liquid chromatography with mass spectrometry. In preferred embodiments, the liquid chromatography is HPLC. One preferred embodiment utilizes HPLC alone or in combination with one or more purification methods such as for example immobilized boronic acid filtration and/or protein precipitation and filtration, to purify E, and/or NE, and/or D in a sample. In another preferred embodiment, the mass spectrometry is tandem mass spectrometry (MS/MS).

In certain preferred embodiments of the methods disclosed herein, mass spectrometry is performed in positive ion mode. Alternatively, mass spectrometry is performed in negative ion mode. Various ionization sources, including for example atmospheric pressure chemical ionization (APCI) or electrospray ionization (ESI), may be used in embodiments of the present invention. In certain preferred embodiments, E, and/or NE, and/or D is measured using a heated ESI probe in positive ion mode.

In preferred embodiments, E ions detectable in a mass spectrometer are selected from the group consisting of positive ions with a mass to charge ratio (m/z) of 166.1±0.50 and 107.0±0.50 NE ions detectable in a mass spectrometer are selected from the group consisting of positive ions with a mass to charge ratio (m/z) of 151.9±0.50 and 107.0±0.50; and D ions detectable in a mass spectrometer are selected from the group consisting of positive ions with a mass to charge ratio (m/z) of 136.9±0.50 and 91.0±0.50. In particularly preferred embodiments, a E precursor ion has m/z of 166.10±0.50, and a fragment ion has m/z of 107.0±0.50; a NE precursor ion has m/z of 151.90±0.50, and a fragment ion has m/z of 107.0±0.50; and a D precursor ion has m/z of 136.90±0.50, and a fragment ion has m/z of 91.0±0.50.

In preferred embodiments, one or more separately detectable internal standards is provided in the sample, the amount of which is also determined in the sample. In these embodiments, all or a portion of both the endogenous E, NE, and D and the one or more internal standards present in the sample are ionized to produce a plurality of ions detectable in a mass spectrometer, and one or more ions produced from each are detected by mass spectrometry.

Preferred internal standards for E, NE, and D are $d_3$-epinephrine ($d_3$-E), $d_6$-norepinephrine ($d_6$-NE), and $d_3$-dopamine ($d_3$-D), respectively. In preferred embodiments, $d_3$-E ions detectable in a mass spectrometer are selected from the group consisting of positive ions with m/z of 169.0±0.50 and 107.0±0.50; $d_6$-NE ions detectable in a mass spectrometer are selected from the group consisting of positive ions with m/z of 158.0±0.50 and 111.0±0.50; and $d_3$-D ions detectable in a mass spectrometer are selected from the group consisting of positive ions with m/z of 139.9±0.50 and 94.0±0.50. In particularly preferred embodiments, $d_3$-E has a precursor ion with m/z of 169.0±0.50 and a fragment ion with m/z of 107.0±0.50; $d_6$-NE has a precursor ion with m/z of 158.0±0.50 and a fragment ion with m/z of 111.0±0.50; and $d_3$-D has a precursor ion with m/z of 139.9±0.50 and a fragment ion with m/z of 94.0±0.50.

In preferred embodiments, the presence or amount of the E, and/or NE, and/or D ions are related to the presence or amount of E, and/or NE, and/or D in a test sample by comparison to references such as $d_3$-epinephrine ($d_3$-E), and/or $d_6$-norepinephrine ($d_6$-NE), and/or $d_3$-dopamine ($d_3$-D).

In certain preferred embodiments, the limit of quantitation (LOQ) of E is within the range of 2.0 µg/L to 20 µg/L, inclusive; preferably within the range of 2.0 µg/L to 10 µg/L, inclusive; preferably within the range of 2.0 µg/L to 5.0 µg/L, inclusive; preferably about 2.0 µg/L.

In certain preferred embodiments, the limit of quantitation (LOQ) of NE is within the range of 5.0 µg/L to 20 µg/L, inclusive; preferably within the range of 5.0 µg/L to 10 µg/L, inclusive; preferably about 5.0 µg/L.

In certain preferred embodiments, the limit of quantitation (LOQ) of D is within the range of 2.0 µg/L to 20 µg/L, inclusive; preferably within the range of 2.0 µg/L to 10 µg/L, inclusive; preferably within the range of 2.0 µg/L to 5.0 µg/L, inclusive; preferably about 5.0 µg/L.

As used herein, unless otherwise stated, the singular forms "a," "an," and "the" include plural reference. Thus, for example, a reference to "a protein" includes a plurality of protein molecules.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected E, NE, and D parent or daughter ions by mass spectrometry. Relative reduction as this term is used does not require that any substance, present with the analyte of interest in the material to be purified, is entirely removed by purification.

As used herein, the term "test sample" refers to any sample that may contain E, NE, or D. As used herein, the term "body fluid" means any fluid that can be isolated from the body of an individual. For example, "body fluid" may include blood, plasma, serum, bile, saliva, urine, tears, perspiration, and the like.

As used herein, the term "solid phase extraction" or "SPE" refers to a process in which a chemical mixture is separated into components as a result of the affinity of components dissolved or suspended in a solution (i.e., mobile phase) for a solid through or around which the solution is passed solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFCC) (sometimes known as high turbulence liquid chromatography (HTLC) or high throughput liquid chromatography).

As used herein, the term "high performance liquid chromatography" or "HPLC" refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography (HTLC) or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*, jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 μm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means 10%. In a preferred embodiment the analytical column contains particles of about 4 μm in diameter.

As used herein, the term "on-line" or "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "sample injection" refers to introducing an aliquot of a single sample into an analytical instrument, for example a mass spectrometer. This introduction may occur directly or indirectly. An indirect sample injection may be accomplished, ter example, by injecting an aliquot of a sample into a HPLC column that is connected to a mass spectrometer in an on-line fashion.

As used herein, the term "same sample injection" with respect to multiple analyte analysis by mass spectrometry means that the ions for two or more different analytes are determined essentially simultaneously by measuring ions for the different analytes from the same (i.e. identical) sample injection.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. Nos. 6,204,500, entitled "Mass Spectrometry From Surfaces," 6,107,623, entitled "Methods and Apparatus for Tandem Mass Spectrometry," 6,268,144, entitled "DNA Diagnostics Based On Mass Spectrometry," 6,124,137, entitled "Surface-Enhanced Photolabile Attachment And Release For Desorption And Detection Of Analytes," Wright et al., *Prostate Cancer and Prostatic Diseases* 1999, 2: 264-76; and Merchant and Weinberger, *Electrophoresis* 2000, 21: 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which abeam of high energy atoms (often Xe or Ar) impacts anon-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which may be heated to prevent condensation and to facilitate solvent evaporation. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+, See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heats causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion and one or more fragment ions are selectively detected.

As used herein, the term "limit of quantification", "limit of quantitation" or "LOQ" refers to the point where measurements become quantitatively meaningful. The analyte response at this LOQ is identifiable, discrete and reproducible with a relative standard deviation (RSD %) of 20% and an accuracy of 80% to 120%.

As used herein, the term "limit of detection" or "LOD" is the point at which the measured value is larger than the uncertainty associated with it. The LOD is the point at which a value is beyond the uncertainty associated with its measurement and is defined as two times the RSD of the mean at the zero concentration.

As used herein, an "amount" of an analyte in a body fluid sample refers generally to an absolute value reflecting the mass of the analyte detectable in volume of body fluid. However, an amount also contemplates a relative amount in comparison to another analyte amount. For example, an amount of analyte in a body fluid can be an amount which is greater than a control or normal level of analyte normally present.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to 0.50 atomic mass unit.

The summary of the invention described above is non-limiting and other features and advantages of the invention will be apparent from the following detailed description of the invention, and from the claims.

DETAILED DESCRIPTION OF THE INVENTION

Figure 1:
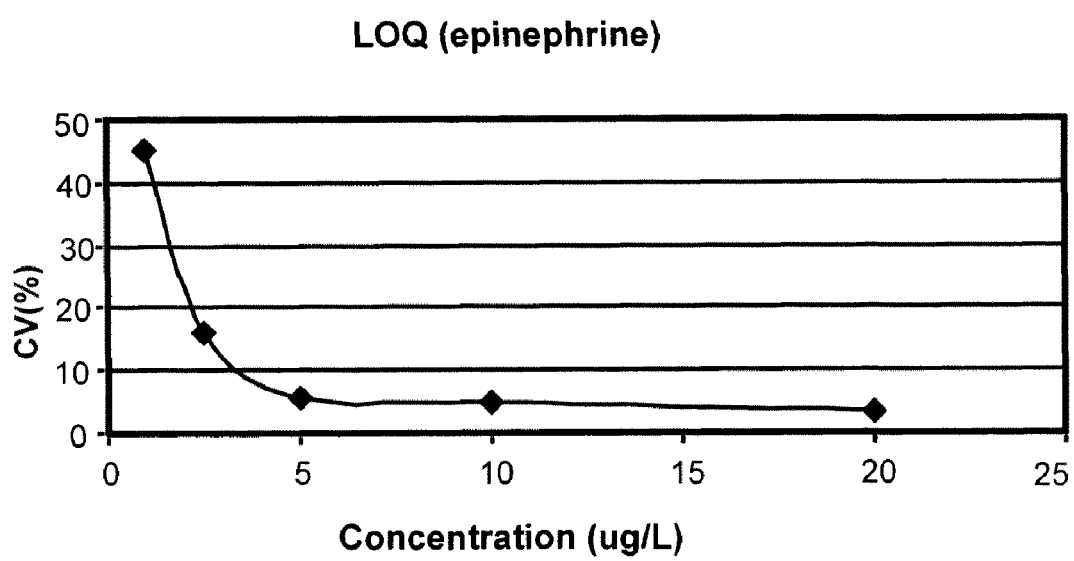
FIGS. 1, 2, and 3 show plots of the coefficient of variation of assays of a blank and five standards used to determine the limit of quantitation of the E, NE, and D assays, respectively, Details are discussed in Example 5.

Methods are presented for measuring the amount of one or more catecholamines from the group consisting of E, NE, and D in a sample. More specifically, mass spectrometric methods are described for detecting in a sample one or more catecholamines from the group consisting of E, NE, and D. Specifically, any one of the catecholamines E, NE, and D in a sample may be detected by mass spectrometry; or any two of E, NE, and D in a sample may be detected by mass spectrometry; or all three of E, NE, and D in a sample may be detected by mass spectrometry. The methods may utilize high performance liquid chromatography (HPLC), to perform a purification of selected analytes, and combine this purification with methods of mass spectrometry (MS), thereby providing a high-throughput assay system for detecting and quantifying one or more catecholamines from the group consisting of E, NE, and D in a sample. The preferred embodiments are particularly well suited for application in large clinical laboratories for automated catecholamine assay.

Suitable samples for use in methods of the present invention include any sample that may contain the analyte of interest. In some preferred embodiments, a sample is a biological sample; that is, an aqueous sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Particularly preferred samples include bodily fluids such as urine, blood, plasma, serum, saliva, cerebrospinal fluid, or tissue samples. Such samples may be obtained, for example, from a patient; that is, a living person, male or female, presenting oneself in a clinical setting for diagnosis, prognosis, or treatment of a disease or condition. The sample is preferably obtained from a patient, for example, a urine specimen; preferably a 24-hour urine specimen. A preservative (i.e., an agent that maintains a pH below about 3, such as 6N HCl) should be added to any urine specimen that is not immediately analyzed because the stability of catecholamines declines as the pH rises, with destruction becoming extremely rapid in an alkaline medium. For catecholamine analysis according to methods of the present invention, a sample volume of about 200 µL is preferred.

Also presented are kits for an E and/or NE and/or D quantitation assay. Such kits comprise one or more internal standards, in amounts sufficient for at least one assay. Typically, the kits will also include instructions recorded in a tangible form (e.g., contained on paper or an electronic medium) for using the packaged reagents for use in a measurement assay for determining the amount of E and/or NE and/or D.

Calibration and QC pools for use in embodiments of the present invention can be prepared using "stripped" human urine (stripped of catecholamines): for example, charcoal-stripped human urine (Goldens West Biologicals, Cat. No. OH2020-C, or equivalent). All sources of human or non-human stripped urine should be checked to ensure that they do not contain measurable amounts of catecholamines.

Sample Preparation for Mass Spectrometry

Samples may be prepared for mass spectrometry by enriching E and/or NE and/or D in the sample by any appropriate method. Enrichment of E and/or NE and/or D relative to other components in the sample (e.g. protein) prior to mass spectrometry may be accomplished by various methods known in the art, including for example, liquid chromatography, filtration, centrifugation, thin layer chromatography (TLC), electrophoresis including capillary electrophoresis, affinity separations including immunoaffinity separations, liquid-liquid or solid phase extraction methods including ethyl acetate or methanol extraction or pretreatment with immobilized boronic acid (via a gel or otherwise), the use of chaotropic agents, or any combination of the above or the like. In some preferred embodiments, samples are pretreated by filtration through and elution from boronic acid gel that has been immobilized on a filter plate, followed by LC, preferably HPLC.

Protein precipitation is another method of preparing a test sample, especially a biological test sample, such as serum, plasma, or urine. Such protein purification methods are well known in the art, for example, Poison et al., *Journal of Chromatography B* 2003, 785:263-275, describes protein precipitation techniques suitable for use in methods of the present invention. Protein precipitation may be used to remove most of the protein from the sample leaving E and/or NE and/or D in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to liquid chromatography and subsequent mass spectrometry analysis. In certain embodiments, the use of protein precipitation such as for example, formic acid protein precipitation, may obviate the need for HTLC or other on-line extraction prior to mass spectrometry or HPLC and mass spectrometry.

Accordingly, in some embodiments, protein precipitation, alone or in combination with one or more purification methods, may be used for enrichment of E and/or NE and/or D prior to mass spectrometry. In these embodiments, the methods may involve (1) performing a protein precipitation of the sample of interest; and (2) loading the supernatant directly onto the LC-mass spectrometer without using on-line extraction or HTLC. Alternatively, the methods may involve (1) performing a protein precipitation of the sample of interest; and (2) loading the supernatant onto a HTLC using on-line extraction for further extraction prior to mass spectrometry. In other embodiments, E and/or NE and/or D may be enriched in a sample by protein precipitation followed by LC, preferably HPLC. In some embodiments, protein precipitation may be one of a series of enrichment processes; for example, protein precipitation may be conducted after filtration through and elution from boronic acid gel, and before LC and mass spectrometry.

One means of sample purification that may be used prior to mass spectrometry is liquid chromatography (LC). Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select HPLC instruments and columns that are suitable for use with E, and/or NE, and/or D. The chromatographic column typically includes a medium i.e., a packing material) to facilitate separation of chemical moieties (i.e., fractionation). The medium may include minute particles. The particles include a bonded surface that interacts with the various chemical moieties to facilitate separation of the chemical moieties. One suitable bonded surface is a hydrophobic bonded surface such as an alkyl bonded, a cyano bonded, or a pentalluorophenylpropyl (F5) surface. Alkyl bonded surfaces may include C-4, C-8, C-12, or C-18 bonded alkyl groups. In preferred embodiments, the column is an F5 column. The chromatographic column includes an inlet port for receiving a sample directly or indirectly from a solid-phase extraction or HTLC column and an outlet port for discharging an effluent that includes the fractionated sample.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be enriched in a sample by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be enriched in a sample by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted with a hydrophobic column chromatographic system. In certain preferred embodiments, a F5 analytical column (e.g., a Discovery HS F5 analytical column from Sigma-Aldrich, Inc. (5 μm particle size, 50×4.6 mm), or equivalent) is used. In certain preferred embodiments, HTLC and/or HPLC are performed using HPLC, Grade 0.1% aqueous formic acid and 1% formic acid in acetonitrile as the mobile phases.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, HTLC may be used for enrichment of E and/or NE and/or D prior to mass spectrometry. In such embodiments, samples may be extracted using an extraction cartridge which captures the analyte, then eluted and chromatographed on a second HTLC column or onto an analytical HPLC column prior to ionization. For example, sample extraction with an HTLC extraction cartridge may be accomplished with a large particle size (50 μm) packed column. Sample eluted off of this column may then be transferred to an HPLC analytical column, such as a F5 analytical column, for further purification prior to mass spectrometry. Because the steps involved in these chromatography procedures may be linked in an automated fashion, the requirement for operator involvement during the purification of the analyte can be minimized. This feature may result in savings of time and costs, and eliminate the opportunity for operator error, Detection and Quantitation by Mass Spectrometry In various embodiments, E and/or NE and/or D present in a test sample may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SEMI), inductively coupled plasma (ICP) and particle beam ionization. The skilled artisan will understand that the choice of ionization method may be determined based on the analyte to be measured, type of sample, the type of detector, the choice of positive versus negative mode, etc.

E and/or NE and/or D may be ionized in positive or negative mode. In preferred embodiments. E and/or NE and/or D is ionized by heated ESI in positive mode. In related preferred embodiments. E and/or NE and/or D ions are in a gaseous state and the inert collision gas is argon or nitrogen; preferably argon.

In mass spectrometry techniques generally, after the sample has been ionized, the positively charged or negatively charged ions thereby created may be analyzed to determine a mass-to-charge ratio, Suitable analyzers for determining mass-to-charge ratios include quadrupole analyzers, ion trap analyzers, and time-of-flight analyzers. Exemplary ion trap methods are described in Bartolucci, et al., *Rapid Commun. Mass Spectrom.* 2000, 14:967-73.

The ions may be detected using several detection modes. For example, selected ions may be detected, i.e. using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g., 90 to 1000 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples, and a standard curve constructed based on ions generated from those standards. Using such a standard curve, the relative abundance of a given ion may be converted into an absolute amount of the original molecule. In certain preferred embodiments, one or more internal standards may be used to generate standard curves for calculating the quantity of E and/or NE and/or D. Methods of generating and using such standard curves are well known in the art and one of ordinary skill is capable of selecting appropriate internal standards. For example, an isotopically labeled catecholamine may be used as an internal standard; in certain preferred embodiments, $d_3$-epinephrine ($d_3$-E) and/or $d_6$-norepinephrine ($d_6$-NE) and/or $d_3$-dopamine ($d_3$-D) may be used as internal standards. Numerous other methods for relating the amount of an ion to the amount of the original molecule will be well known to those of ordinary skill in the art.

One or more steps of the presented methods may be performed using automated machines. In certain embodiments, one or more purification steps are performed on-line, and more preferably all of the purification and mass spectrometry steps may be performed on-line.

In certain embodiments, such as MS/MS, where precursor ions are isolated for further fragmentation, collision activation dissociation is often used to generate the fragment ions for further detection. In CAD, precursor ions in energy through collisions with an inert gas, and subsequently fragment by a process referred to as "unimolecular decomposition." Sufficient energy must be deposited in the precursor ion so that certain bonds within the ion can be broken due to increased vibrational energy.

In particularly preferred embodiments, E and/or NE and/or D are quantified in a sample using MS/MS as follows. E and/or NE and/or D in samples are first filtered through and eluted from immobilized boronic acid gel. The resulting eluent is then subjected to liquid chromatography, preferably HPLC. The flow of liquid solvent from the chromatographic column enters the heated ESI probe of an MS/MS analyzer and the analytes ionized. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios of E or NE or D. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral argon gas molecules and fragment. This process is called collision activated dissociation (CAD). The fragment ions generated are passed into quadrupole 3 (Q3), where the fragment ions are selected while other ions are eliminated. During analysis of a single sample, Q1 and/or Q3 may be adjusted such that mass/charge ratios of one or more precursor ion/fragment ion pairs specific to one catecholamine is first selected, followed at some later time by the selection of mass/charge ratios of one or more precursor ion/fragment ion pairs specific to a second catecholamine, optionally followed at some later time by the selection of mass/charge ratios of one or more precursor ion/fragment ion pairs specific to a third catecholamine. In particularly preferred embodiments, mass to charge ratios of precursor/fragment ion pairs specific to E, mass to charge ratios of precursor/fragment ion pairs specific to NE, and mass to charge ratios of precursor/fragment ion pairs specific to D are detected during analysis of a single sample, although the sequence of detection may occur in any order.

The methods may involve MS/MS performed in either positive or negative ion mode; preferably positive ion mode. Using standard methods well known in the art, one of ordinary skill is capable of identifying one or more fragment ions of a particular precursor ion of E and/or NE and/or D that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC methods. The areas under the peaks corresponding to particular ions, or the amplitude of such peaks, are measured and the area or amplitude is correlated to the amount of the analyte of interest. In certain embodiments, the area under the curves, or amplitude of the peaks, for fragment ion(s) and/or precursor ions are measured to determine the amount of analyte or analytes detected. As described above, the relative abundance of a given ion or parent/fragment ion pair may be converted into an absolute amount of an original analyte, e.g., E or NE or D, using calibration standard curves based on peaks of one or more ions of an internal molecular standard, such as $d_3$-epinephrine ($d_3$-E) and/or $d_6$-norepinephrine ($d_6$-NE) and/or $d_3$-dopamine ($d_3$-D).

The following examples serve to illustrate the invention. These examples are in no way intended to limit the scope of the methods.

EXAMPLES

Example 1

Urine Sample and Reagent Preparation 24-hour urine specimens (typically greater than 50 mL) were collected in a clean container to which 25 mL of 6N HCl was added as a preservative to maintain a pH below 3. After collection, the specimens were mixed well and the total volume recorded. Samples of about 10 mL to 50 mL were then collected from each acidified urine specimen and frozen for storage and transport.

A mixed standard stock solution of 1.0 mg/mL E, 1.0 mg/mL NE, and 1.0 mg/mL D in 1 g/L sodium metabisulfite in 83 mmol/L acetic acid solution. This solution was prepared by dissolving 10 mg each of E and NE (Sigma Chemical Company, Cat. Nos. 02250-5G, A7257-1G, respectively, or equivalents), and 12.4 mg dopamine hydrochloride (Sigma Chemical Company, Cat. No. 56610-25G, or equivalent) in 10 mL of 1 g/L sodium metabisulfite in 83 mmol/L acetic acid solution. A mixed standard working solution of 1 μg/mL in stripped human urine (Golden West Biologicals, Cat. No. OH2020-C, or equivalent, with pH adjusted to about 2.5) was prepared in a volumetric flask from diluting the mixed standard stock solution by 1:1000.

A mixed internal standard solution of 3.0 mg/L $d_3$-E, 3.0 mg/L $d_6$-NE, and 3.0 mg/L $d_3$-D (CDN, Cat. Nos, D-1702, D-6633, and 6634, or equivalents) in 1 g/L sodium metabisulfite in 83 mmol/L acetic acid solution was also prepared.

Example 2

Extraction of Catecholamines from Samples with Immobilized Boronic Acid Gel

Immobilized boronic acid gel was prepared for sample extraction by pipetting 500 μL of 0.2 M ammonium acetate into each well of a PVDF 96-well filter plate on top of a 2 mL 96-square well plate. After the ammonium acetate was allowed to sit for 2-5 minutes, excess buffer was drained with a System 96 Processor II (SPEware Corp., Product ft 288-0001) and discarded. Another 500 µL of 0.2 M ammonium acetate, followed by 100 µL of immobilized boronic acid gel, was then added to each well and the resulting mixture allowed to sit for 2-5 minutes. The excess liquid was again drained with the 96 Processor II and discarded. A final 500 µL of 0.2 M ammonium acetate was then added and let sit for 2-5 minutes, before also being drained with the 96 Processor II and discarded.

All frozen samples and standards were thawed, and 200 µL of each standard, control, and patient samples were pipetted into labeled test tubes along with 20 µL of the mixed internal standard solution. 100 µL of 1 M TRIS buffer and 100 µL of 0.2 M ammonium acetate were then added to each test tube. The resulting mixtures were immediately transferred to the wells of the 96-well filter plate with immobilized boronic acid gel and allowed to incubate for about 15 minutes. The 96 Processor II was then used to completely drain and discard the flow-through. The filter plate was transferred to a new 96-well plate for analyte collection.

The samples were then washed by adding 500 µL of 0.2 M ammonium acetate, letting the solution sit for 2 to 5 minutes, and using the 96 Processor II to completely drain and discard the flow-through. A second wash was then conducted with 500 µL of 0.05 M formic acid for 1 to 2 minutes before draining.

200 µL of 0.2 M formic acid was then added to each well, and incubated for about 45 minutes. After incubation, the well plate was centrifuged for 10 minutes at 5000 rpm (at approximately 13-18° C.) to collect analytes in the filtrate.

Example 3

Extraction of Analytes with Liquid Chromatography

50 µL of an above prepared sample was automatically injected into a Discovery HS F5 analytical column from Sigma-Aldrich, Inc. (5 µm particle size, 50×4.6 mm). A binary HPLC gradient was applied to the analytical column, to separate E, NE, and D from other analytes contained in the sample. Mobile phase A was 0.1% formic acid in water and mobile phase B was 0.1% formic acid in acetonitrile. The HPLC gradient started with a 1% organic gradient which ramped to 30% in approximately 1.25 minutes. The separated sample was then subjected to MS/MS for quantitation of E, NE, and D.

Example 4

Detection and Quantitation of Catecholamines by MS/MS

MS/MS was performed using a Finnigan TSQ Quantum Ultra MS/MS system (Thermo Electron Corporation). The following software programs all from ThermoElectron were used in the Examples described herein: Quantum Tune Master V 1.2 or newer, Xcalibur V 1.4 SR1 or newer, TSQ Quantum 1.4 or newer, and LCQuan V 2.0 with SP1 or newer. Liquid solvent/analyte exiting the analytical column flowed to the heated nebulizer interface of a Thermo Finnigan MS/MS analyzer. The solvent/analyte mixture was converted to vapor in the heated tubing of the interface. Analytes in the nebulized solvent were ionized by heated ESI.

Ions passed to the first quadrupole (Q1), which selected ions with a mass to charge ratio of parent ions generated from one of the analytes. Ions entering quadrupole 2 (Q2) collided with argon gas to generate ion fragments, which were passed to quadrupole 3 (Q3) for further selection. After measurement of ions indicative of one of the analytes, Q1 was adjusted so that ions with a mass to charge ratio of parent ion from a second analyte were selected. These ions were collided with argon gas in Q2, and the ion fragments passed to Q3 for further selection. After measurement of these ions, Q1 was adjusted so that ions with a mass to charge ratio of parent ion from a third analyte were selected. These ions were collided with argon gas in Q2, and the ion fragments passed to Q3 for further selection. Simultaneously, the same process using isotope dilution mass spectrometry was carried out with internal standards, $d_3$-epinephrine ($d_3$-E) and/or $d_6$-norepinephrine ($d_6$-NE) and/or $d_3$-dopamine ($d_3$-D). The following mass transitions were used for detection and quantitation of E, NE, and D (and their corresponding internal standards) during validation on positive polarity from the same sample injection.

TABLE 1

Mass Transitions for Catecholamines (Positive Polarity)

| Analyte | Precursor Ion (m/z) | Product Ion (m/z) | Collision Energy (V) |
|---|---|---|---|
| Epinephrine | 166.1 | 107.0 | 17 |
| $d_3$-Epinephrine | 169.0 | 107.0 | 18 |
| Norepinephrine | 151.9 | 107.0 | 16 |
| $d_6$-Norepinephrine | 158.0 | 111.0 | 17 |
| Dopamine | 136.9 | 91.0 | 17 |
| $d_3$-Dopamine | 139.9 | 94.0 | 17 |

Example 4

Intra-Assay and Inter-Assay Precision and Accuracy

Three quality control (QC) pools were prepared from Normal and Abnormal Urine Controls (Bio-Rad, Cat. No. 0930-25 and 0395-25). Normal and Abnormal Urine controls were reconstituted with 10 mL of 0.05 N HCl, while a Medium control was prepared by mixing an equal volume of reconstituted Normal and Abnormal controls. The reconstituted solutions are stable for approximately 7 days at about 2-8° C.

Twelve aliquots from each of the three QC pools were analyzed in a single assay to determine the coefficient of variation (CV (%)) of a sample within an assay. The following values were determined:

TABLE 2

Intra-Assay Variation and Accuracy

| Replicate | Epinephrine (µg/L) | | | Norepinephrine (µg/L) | | | Dopamine (µg/L) | | |
|---|---|---|---|---|---|---|---|---|---|
| | Low | Med | High | Low | Med | High | Low | Med | High |
| 1 | 13.9 | 48.0 | 77.4 | 50.5 | 118.0 | 198.9 | 113.2 | 335.1 | 592.8 |
| 2 | 14.2 | 46.0 | 83.1 | 48.8 | 112.9 | 198.4 | 110.5 | 326.5 | 553.4 |
| 3 | 14.2 | 47.9 | 77.3 | 49.3 | 125.1 | 190.0 | 113.0 | 327.6 | 528.8 |
| 4 | 15.1 | 46.4 | 85.1 | 50.0 | 119.7 | 191.5 | 115.1 | 330.6 | 589.2 |
| 5 | 14.8 | 47.0 | 80.4 | 48.8 | 121.6 | 183.0 | 110.0 | 335.1 | 554.5 |
| 6 | 13.4 | 46.3 | 82.6 | 50.4 | 123.7 | 209.4 | 107.8 | 351.5 | 545.3 |
| 7 | 13.7 | 48.7 | 80.5 | 48.3 | 123.2 | 187.0 | 111.9 | 338.5 | 597.5 |
| 8 | 13.7 | 45.1 | 78.1 | 49.3 | 124.3 | 186.0 | 106.9 | 335.6 | 575.2 |
| 9 | 13.8 | 48.7 | 84.1 | 50.8 | 124.5 | 193.4 | 108.8 | 334.0 | 562.3 |

TABLE 2-continued

Intra-Assay Variation and Accuracy

| Repli-cate | Epinephrine (μg/L) | | | Norepinephrine (μg/L) | | | Dopamine (μg/L) | | |
|---|---|---|---|---|---|---|---|---|---|
| | Low | Med | High | Low | Med | High | Low | Med | High |
| 10 | 14.2 | 44.8 | 74.7 | 47.8 | 125.3 | 197.6 | 108.1 | 327.4 | 545.2 |
| 11 | 14.5 | 46.6 | 82.4 | 49.5 | 125.4 | 187.1 | 113.1 | 328.6 | 521.1 |
| 12 | 14.0 | 62.5* | 82.6 | 49.7 | 120.7 | 205.1 | 117.2 | 333.7 | 565.2 |
| Mean | 14.1 | 46.9 | 80.7 | 49.4 | 122.0 | 194.0 | 111.3 | 333.7 | 560.9 |
| STD | 0.5 | 1.3 | 3.2 | 0.9 | 3.7 | 8.1 | 3.2 | 6.8 | 24.5 |
| CV (%) | 3.5 | 2.9 | 4.0 | 1.8 | 3.1 | 4.2 | 2.8 | 2.0 | 4.4 |
| Target value | 15.5 | 47.9 | 76.7 | 52.4 | 128.7 | 208.8 | 109.7 | 343.3 | 592.3 |
| Accuracy (%) | 91.1 | 97.8 | 105.2 | 94.3 | 94.8 | 92.9 | 101.5 | 97.2 | 94.7 |

* = Data point lies outside 3 STD from mean, and was omitted as outlier.

Aliquots from each of the three QC pools were assayed seven times over the course of thirty five days to determine the coefficient of variation (CV (%)) between assays. The following values were determined:

TABLE 3

Inter-Assay Variation and Accuracy

| Day | Epinephrine (μg/L) | | | Norepinephrine (μg/L) | | | Dopamine (μg/L) | | |
|---|---|---|---|---|---|---|---|---|---|
| | Low | Med | High | Low | Med | High | Low | Med | High |
| 1 | 14 | 45 | 75 | 50 | 120 | 192 | 117 | 334 | 571 |
| | 15 | 47 | 80 | 50 | 122 | 185 | 113 | 331 | 589 |
| 6 | 16 | 50 | 81 | 51 | 119 | 187 | 116 | 333 | 559 |
| | 16 | 47 | 78 | 50 | 120 | | 107 | 332 | |
| 28 | 16.9 | 45.2 | 77.7 | 52.1 | 121.8 | 192.1 | 111.8 | 326.8 | 559.3 |
| | 13 | 42.4 | 76.6 | 52.7 | 117.8 | 187.1 | 110.7 | 332.3 | 559.9 |
| | 12.6 | | 73.4 | 51.5 | | 178.9 | 107 | | 534.8 |
| 29 | 13.9 | 40.9 | 72.3 | 52.6 | 119.1 | 182 | 110.2 | 321 | 556.4 |
| | 11.7 | 41 | 76.8 | 48.1 | 116.8 | 183.1 | 111.1 | 318.6 | 545.7 |
| | 13.5 | 44.4 | 75.8 | 52.1 | 123.3 | 182.1 | 102 | 326.8 | 531.3 |
| | 12.3 | 42.1 | 75.4 | 50.3 | 116.1 | 178.4 | 106.6 | 318.4 | 541.5 |
| | 13.2 | 40.8 | 70.3 | 54 | 117.2 | 180.1 | 108 | 346.8 | 544.8 |
| 30 | 14.4 | 49.2 | 76.5 | 50.7 | 115.9 | 190.2 | 107.5 | 319.3 | 550.7 |
| | 15.4 | 46.9 | 83.4 | 53.5 | 125.4 | 196.4 | 114.2 | 327.3 | 554.1 |
| | 13.8 | 48.6 | 82.8 | 48.6 | 121 | 186.5 | 106.6 | 326.2 | 530.2 |
| | 13.8 | 50.7 | 84.2 | 53 | 128.3 | 195.8 | 106.9 | 327.8 | 542.4 |
| | 14.9 | 43.2 | 77.2 | 50.1 | 112.9 | 181.6 | 108.9 | 318 | 545.5 |
| 33 | 13.7 | 46.9 | 77.5 | 53.8 | 116 | 182.8 | 115.3 | 331.3 | 541.5 |
| | 13.7 | 45.3 | 78.9 | 49 | 114.1 | 173.3 | 115.6 | 328.9 | 536.7 |
| | 14.4 | 45.7 | 78.1 | 50.6 | 113.1 | 183.9 | 114.1 | 331.7 | 538.8 |
| 35 | 14.3 | 46.6 | | 52.1 | 119 | | 104.8 | 328.9 | |
| | 14.8 | 47.4 | 78.8 | 48.4 | 116.4 | 185.4 | 105 | 324.6 | 541.8 |
| | 14.4 | 48.6 | 83 | 54.7 | 113.5 | 189 | 110.1 | 330.5 | 547.8 |
| | 14.5 | 46.1 | 83.4 | 53.7 | 114.6 | 186.1 | 111.3 | 335.2 | 562 |
| Mean | 14.1 | 45.3 | 77.4 | 51.4 | 118.4 | 185.4 | 110.0 | 331.5 | 551.0 |
| STD | 1.4 | 3.3 | 3.9 | 1.9 | 4.0 | 5.7 | 4.0 | 2.5 | 15.1 |
| CV (%) | 10.0 | 7.4 | 5.0 | 3.7 | 3.4 | 3.1 | 3.7 | 0.8 | 2.7 |
| Target value | 15.4 | 47.6 | 76.2 | 50.0 | 122.7 | 199.1 | 109.7 | 343.3 | 592.3 |
| Accuracy (%) | 91.8 | 95.1 | 101.6 | 102.7 | 96.5 | 93.1 | 100.3 | 96.6 | 93.0 |

As seen in Tables 1 and 2, all pools met the acceptable reproducibility requirements of ≤15% CV; with accuracies for all pools between 90-110%.

Example 5

Analytical Sensitivity: Limit of Detection (LOD) and Limit of Quantitation (LOQ)

Figure 2:
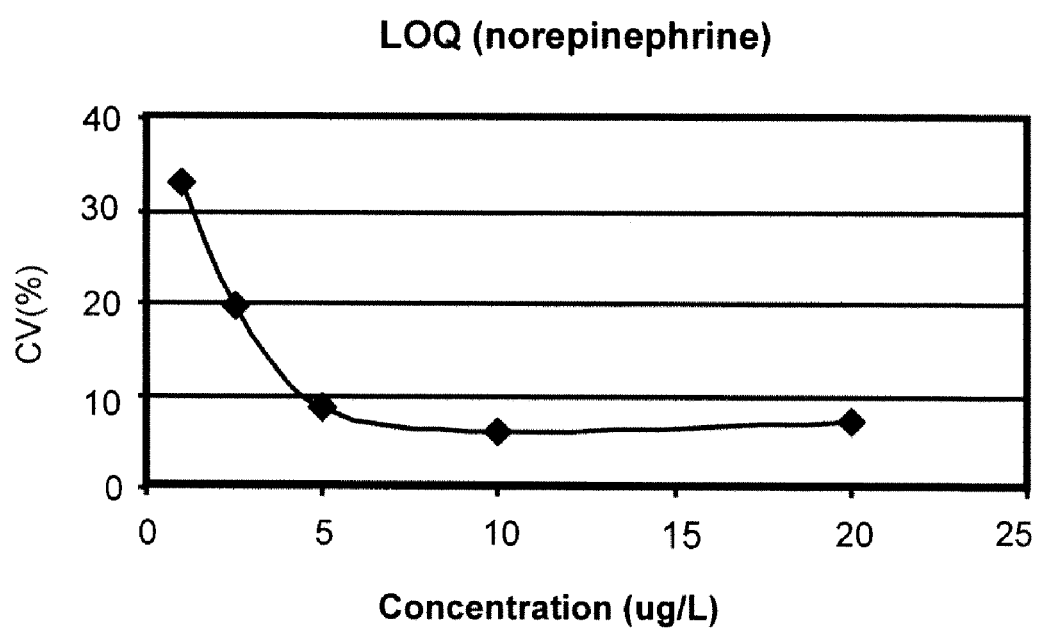
Figure 3:
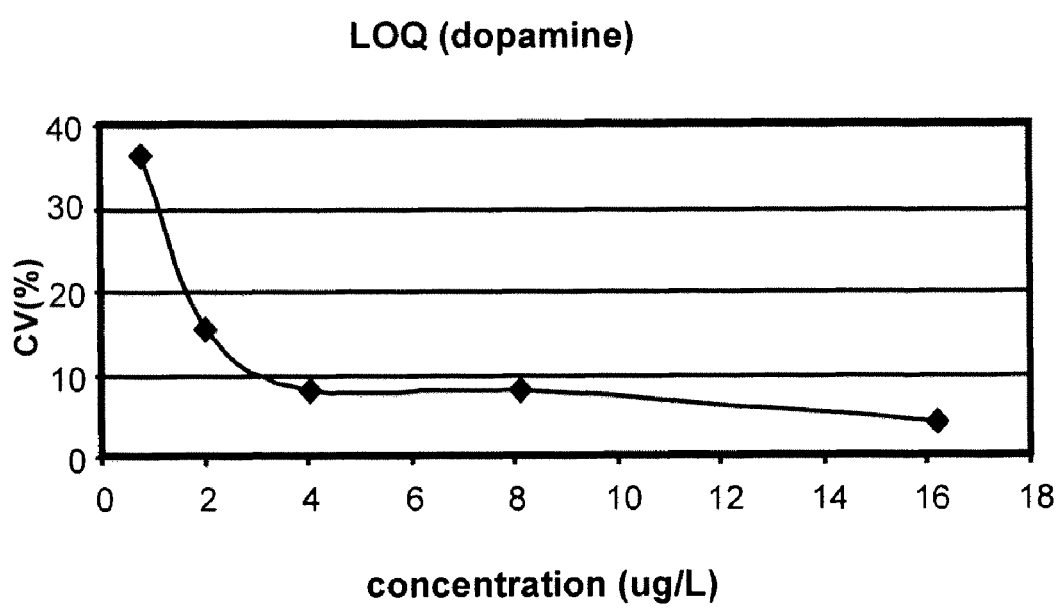

The LOQ is the point where measurements become quantitatively meaningful. The analyte response at this LOQ is identifiable, discrete and reproducible with a precision of 20% and an accuracy of 80% to 120%. The LOQ was determined by assaying samples at concentrations close to the expected LOQ and determining the reproducibility (four replicates each at 1, 2.5, 5.0, 10.0, and 20.0 μg/L E, NE, and D) then determining the CV. The results were plotted for E, NE, and D (shown in FIGS. 1-3, respectively) and the LOQ of each analyte was determined from the curves to be 2 μg/L for E, 2 μg/L for D, and 5 μg/L for NE.

The LOD is the point at which a value is beyond the uncertainty associated with its measurement and is defined as three standard deviations from the zero concentration. To determine the LOQ for detection of N, NE, and D, blank samples of stripped urine were run in twelve replicates. The results of these assays were statistically analyzed with LODs calculated as 0.65 μg/L for E, 1.17 μg/L NE, and 0.44 μg/L for D.

Example 6

Assay Reportable Range and Linearity

Figure 4:
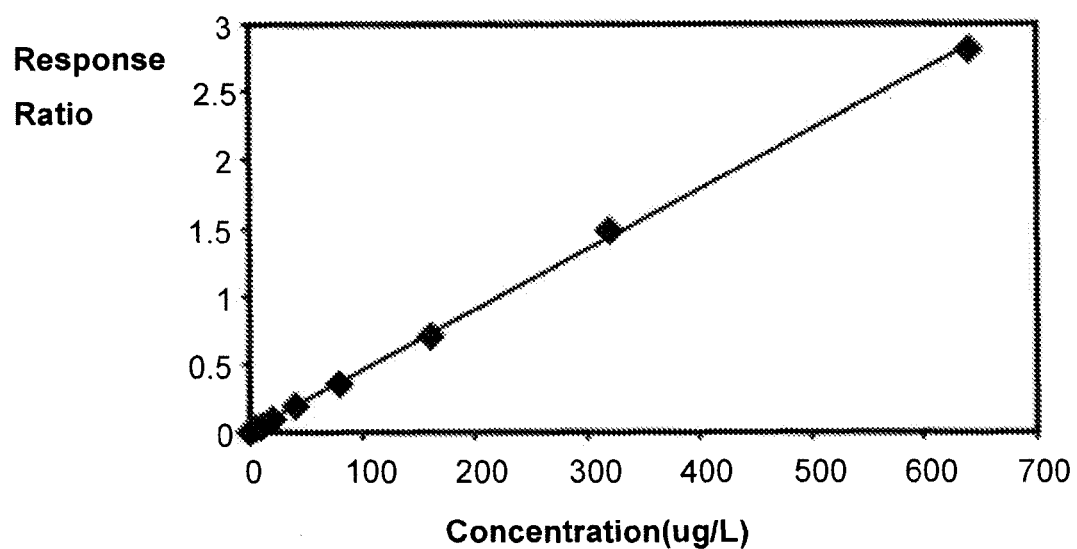
FIGS. 4, 5, and 6 show the linearity of the quantitation of E, NE, and D, respectively, in serially diluted stock samples using an LC-MS/MS assay. Correlation values ($R^2$) for E, NE, and D derived from these studies were 0.9996, 0.9998, and 0.9997, respectively. Details are described in Example 6.
Figure 5:
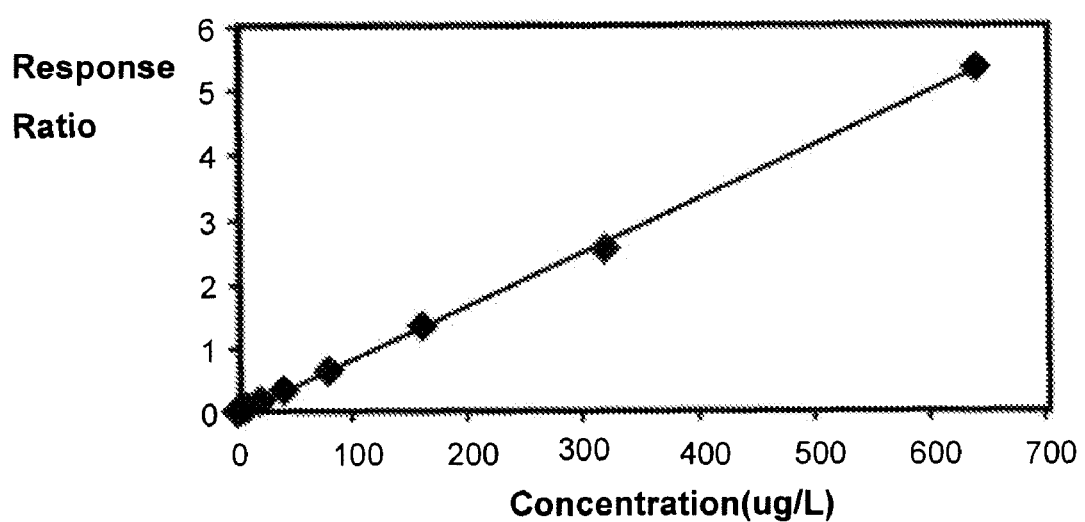
Figure 6:
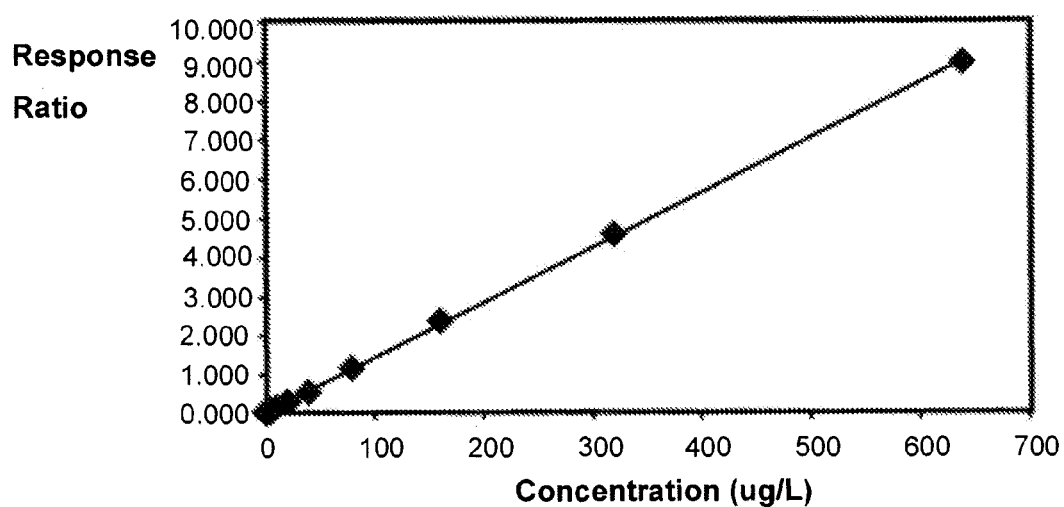

To establish the linearity of E, NE, and D detection, one blank assigned as zero standard and eight spiked human urine standards at concentrations ranging from 5.0 to 640 μg/L were assayed. The correlation values of the concentration range tested was 0.9996 for E, 0.9998 for NE, and 0.9997 for D. Graphs showing the linearity of the standard curves up to 640 μg/L for the three analytes are shown in FIGS. 4-6, respectively.

Example 7

Assay Specificity

Assay specificity was evaluated against 16 similar analytes: Hydralazine hydrochloride, Clonidine hydrochloride Glipizide, Atenolol, Lisinopril, Felodipine, Cyclobenzaprine hydrochloride, Acetaminophen, Labetalol hydrochloride, (S)-(+)-Ibuprofen. Cyclobenzaprine hydrochloride, Propanol hydrochloride, Tramadol hydrochloride, Simvastatin, Caffeine, (S)-(−)-Carbidopa and 3,4-Dihydroxy-L-Phynl-alanine. Cross-reactivity was determined for each analyte by analyzing a sample for D, E, and NE before and after spiking the sample to 500 μg/L of a cross-reactivity analyte. A significant increase in the observed dose of D, E, or NE after the sample has been spiked indicates cross-reactivity. The only drug with significant cross-reactivity was 3,4-Dihydroxy-L-Phenyl-alanine for NE, at less than 8%. The results of this study are presented in Tables 4.

TABLE 4

Analyte Specificity of D, E, and NE

| Analyte Tested for Cross-Reactivity | Observed change in dose (ug/L) | | | Cross-Reactivity (%) | | |
|---|---|---|---|---|---|---|
| | Dop. | Epi. | Norepi. | Dop. | Epi. | Norepi. |
| Hydralazine HCl | 1.3 | 0.8 | <0 | 0.26 | 0.16 | ND |
| Clonidine HCl | <0 | 1 | <0 | ND | 0.20 | ND |
| Glipizide | 2.3 | <0 | <0 | 0.46 | ND | ND |
| Atenolol | 0.1 | <0 | 0.5 | 0.02 | ND | 0.10 |
| Lisinopril | 1.1 | 0.5 | 0.5 | 0.22 | 0.10 | 0.10 |
| Felodipine | 0.3 | 0.4 | <0 | 0.06 | 0.08 | ND |
| Cyclobenzaprine HCl | 0.7 | <0 | <0 | 0.14 | ND | ND |
| Labetalol HCl | 0.2 | <0 | <0 | 0.04 | ND | ND |
| Tramadol HCl | 1.6 | 0.4 | <0 | 0.32 | 0.08 | ND |
| Simvastatin | 4.5 | 1.6 | <0 | 0.90 | 0.32 | ND |
| Caffeine | <0 | <0 | <0 | ND | ND | ND |
| (S)-(+)-Ibuprofen | 1.1 | 0.9 | <0 | 0.22 | 0.18 | ND |
| Propranolol HCl | <0 | <0 | <0 | ND | ND | ND |
| Acetaminophen | 0.2 | 0.5 | <0 | 0.04 | 0.10 | ND |
| (S)-(−)-Carbidopa | 1.6 | 0.4 | <0 | 0.32 | 0.08 | ND |
| 3,4-Dihydroxy-L-phenyl-alanine | 0.4 | <0 | 39 | 0.08 | ND | 7.80 |

Example 8

Recovery Studies

Samples were prepared from five different patient sample pools with values within the reportable ranges for E, NE and D for recovery studies. Equal volumes of each pool were mixed with spiked stripped human urine at 0 μg/L, 160 μg/L, 320 μg/L, and 640 μg/L each of E, NE, and D. Thus, the expected concentration of each sample for recovery studies was calculated as (concentration of the patient sample pool+ concentration of spiked human urine)/2. Results of these studies are presented in Tables 5-7 for E, NE, and D, respectively. All recoveries were acceptable, i.e., within the range of 80% to 120%.

TABLE 5

Recovery Studies for E

| Sample | Expected value (ug/L) | Observed value (ug/L) | Recovery (%) |
|---|---|---|---|
| Pool1 + 0 ug/L | not applicable | 5 | |
| Pool1 + 160 ug/L | 85 | 82.4 | 97 |
| Pool1 + 320 ug/L | 165 | 159 | 96 |
| Pool1 + 640 ug/L | 325 | 317 | 98 |
| Pool2 + 0 ug/L | not applicable | 6 | |
| Pool2 + 160 ug/L | 86 | 93 | 108 |

TABLE 5-continued

Recovery Studies for E

| Sample | Expected value (ug/L) | Observed value (ug/L) | Recovery (%) |
|---|---|---|---|
| Pool2 + 320 ug/L | 166 | 167 | 101 |
| Pool2 + 640 ug/L | 326 | 320 | 98 |
| Pool3 + 0 ug/L | not applicable | 7 | |
| Pool3 + 160 ug/L | 87 | 83 | 96 |
| Pool3 + 320 ug/L | 167 | 154 | 92 |
| Pool3 + 640 ug/L | 327 | 322 | 99 |
| Pool4 + 0 ug/L | not applicable | 9 | |
| Pool4 + 160 ug/L | 89 | 85 | 96 |
| Pool4 + 320 ug/L | 169 | 158 | 94 |
| Pool4 + 640 ug/L | 329 | 314 | 96 |
| Pool5 + 0 ug/L | not applicable | 7 | |
| Pool5 + 160 ug/L | 87 | 89 | 102 |
| Pool5 + 320 ug/L | 167 | 152 | 91 |
| Pool5 + 640 ug/L | 327 | 308 | 94 |

TABLE 6

Recovery Studies for NE

| Sample ID | Expected value (ug/L) | Observed value (ug/L) | Recovery (%) |
|---|---|---|---|
| (Pool1 + 0 ug/L)/2 | not applicable | 35 | |
| (Pool1 + 160 ug/L)/2 | 115 | 117 | 102 |
| (Pool1 + 320 ug/L)/2 | 195 | 192 | 98 |
| (Pool1 + 640 ug/L)/2 | 355 | 332 | 94 |
| (Pool2 + 0 ug/L)/2 | not applicable | 37 | |
| (Pool2 + 160 ug/L)/2 | 117 | 123 | 105 |
| (Pool2 + 320 ug/L)/2 | 197 | 203 | 103 |
| (Pool2 + 640 ug/L)/2 | 357 | 349 | 98 |
| (Pool3 + 0 ug/L)/2 | not applicable | 26 | |
| (Pool3 + 160 ug/L)/2 | 106 | 110 | 104 |
| (Pool3 + 320 ug/L)/2 | 186 | 180 | 97 |
| (Pool3 + 640 ug/L)/2 | 346 | 328 | 95 |
| (Pool4 + 0 ug/L)/2 | not applicable | 53 | |
| (Pool4 + 160 ug/L)/2 | 133 | 135 | 102 |
| (Pool4 + 320 ug/L)/2 | 213 | 212 | 100 |
| (Pool4 + 640 ug/L)/2 | 373 | 376 | 101 |
| (Pool5 + 0 ug/L)/2 | not applicable | 52 | |
| (Pool5 + 160 ug/L)/2 | 132 | 134 | 102 |
| (Pool5 + 320 ug/L)/2 | 212 | 215 | 101 |
| (Pool5 + 640 ug/L)/2 | 372 | 348 | 94 |

TABLE 7

Recovery Studies for D

| Sample ID | Expected value (ug/L) | Observed value (ug/L) | Recovery (%) |
|---|---|---|---|
| (Pool1 + 0 ug/L)/2 | not applicable | 80 | |
| (Pool1 + 160 ug/L)/2 | 160 | 161 | 101 |
| (Pool1 + 320 ug/L)/2 | 240 | 237 | 99 |
| (Pool1 + 640 ug/L)/2 | 400 | 403 | 101 |
| (Pool2 + 0 ug/L)/2 | not applicable | 105 | |
| (Pool2 + 60 ug/L)/2 | 185 | 205 | 111 |
| (Pool2 + 320 ug/L)/2 | 265 | 254 | 96 |
| (Pool2 + 640 ug/L)/2 | 425 | 417 | 98 |
| (Pool3 + 0 ug/L)/2 | not applicable | 52 | |
| (Pool3 + 60 ug/L)/2 | 132 | 128 | 97 |
| (Pool3 + 320 ug/L)/2 | 212 | 203 | 96 |
| (Pool3 + 640 ug/L)/2 | 372 | 350 | 94 |
| (Pool4 + 0 ug/L)/2 | not applicable | 133 | |
| (Pool4 + 160 ug/L)/2 | 213 | 212 | 100 |
| (Pool4 + 320 ug/L)/2 | 293 | 282 | 96 |
| (Pool4 + 640 ug/L)/2 | 453 | 431 | 95 |
| (Pool5 + 0 ug/L)/2 | not applicable | 142 | |
| (Pool5 + 160 ug/L)/2 | 222 | 222 | 100 |
| (Pool5 + 320 ug/L)/2 | 302 | 301 | 100 |
| (Pool5 + 640 ug/L)/2 | 462 | 442 | 96 |

Example 10

Comparison of HPLC-MS and HPLC with
Electrochemical Detection Studies

Figure 7:
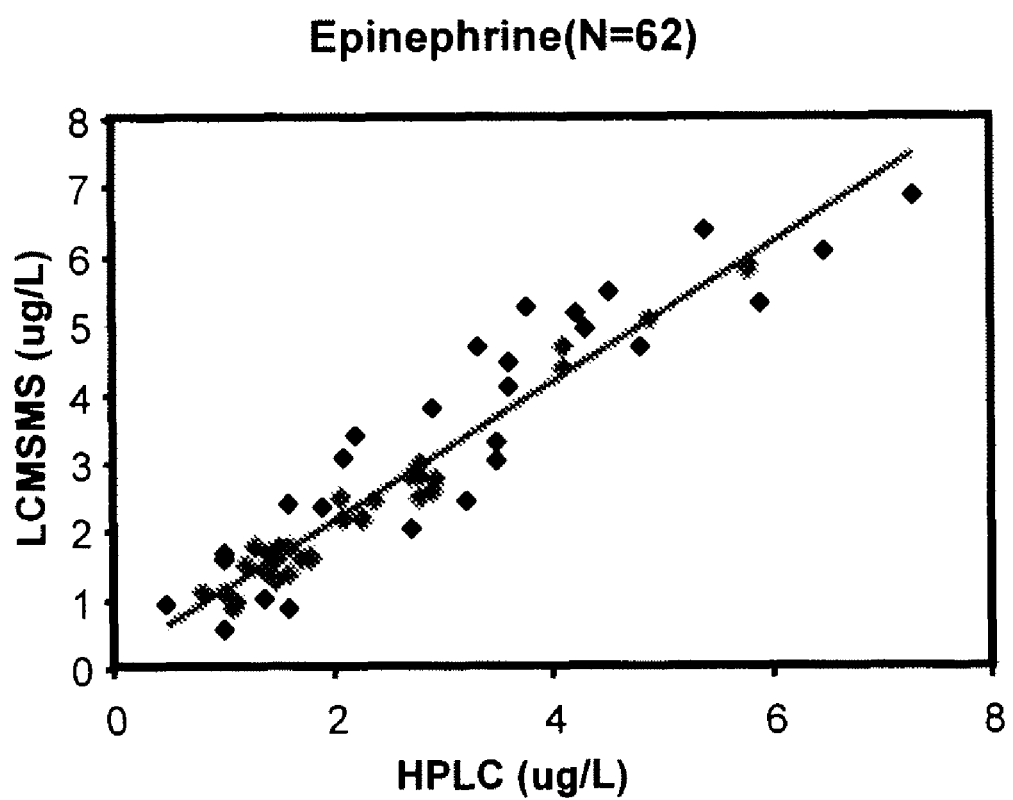
FIGS. 7, 8, and 9 show the correlation of E, NE, and D determination by an exemplary HPLC-MS method of the present invention with E, NE, and D determination by a reference HPLC/electrochemical detection method, respectively. The correlations shown in FIGS. 7, 8, and 9 were determined by linear regression. Details are described in Example 10.
Figure 8:
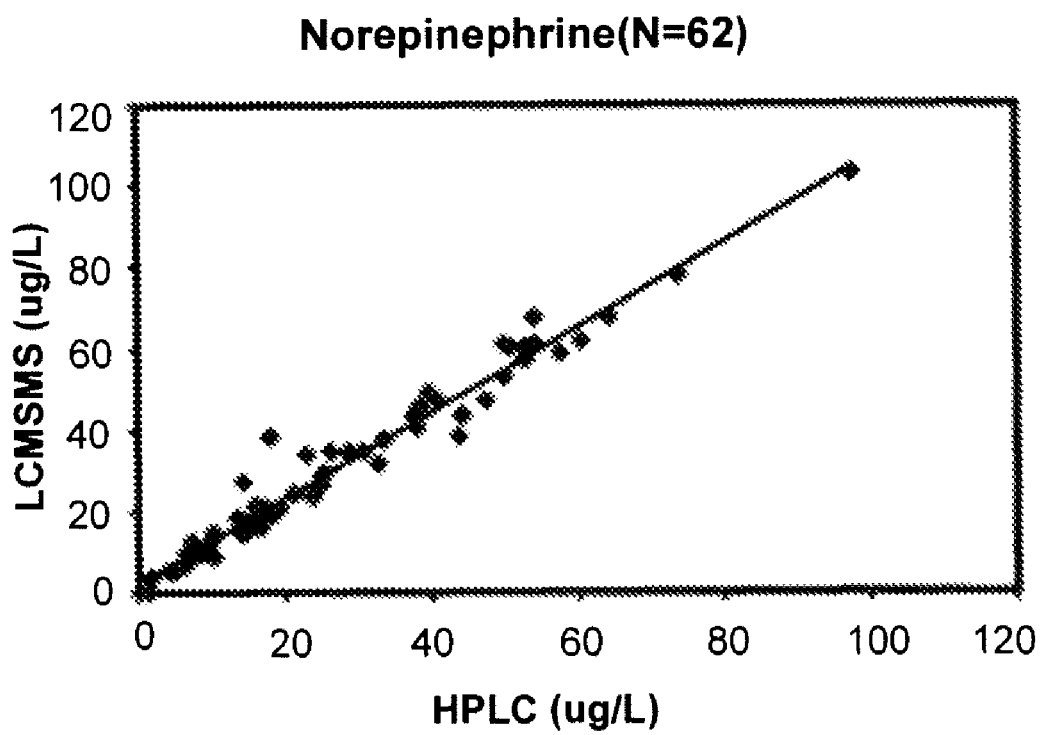
Figure 9:
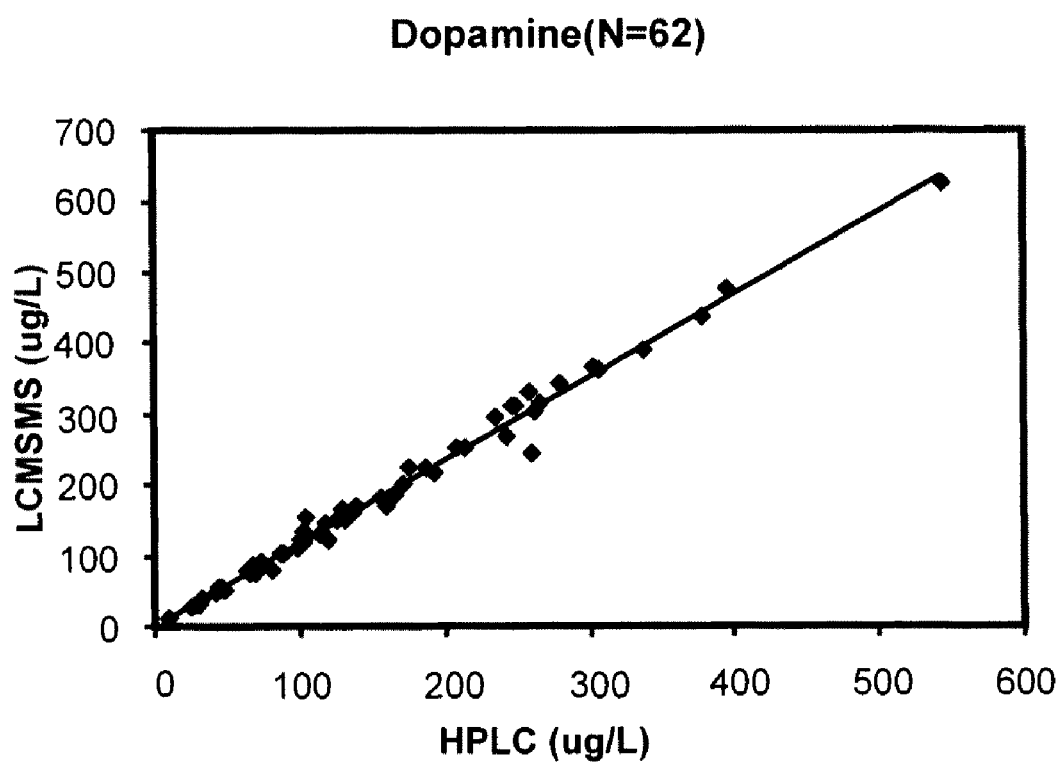

A comparison study was performed using 62 patient samples covering the reportable range, assayed by the presently presented methods with a HPLC/electrochemical detection method. Correlation was determined by linear regression analysis (shown in FIGS. 7-9 for E. NE, and D, respectively). The correlation coefficients for linear regression analysis were 0.9037, 0.9633, and 0.9893 for E, NE, and D, respectively.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining in a urine sample the amount of one or more analytes selected from the group consisting of epinephrine, norepinephrine, and dopamine, the method comprising:
   a. subjecting the sample to electrospray ionization (ESI) under conditions suitable to produce one or more ions detectable by mass spectrometry; wherein:
      i. if one of the one or more analytes is epinephrine, said ionization comprises generating ions with a mass to charge ratio of $166.1\pm0.50$;
      ii. if one of the one or more analytes is norepinephrine, said ionization comprises generating ions with a mass to charge ratio of $151.9\pm0.50$; and
      iii. if one of said one or more analytes is dopamine, said ionization comprises generating ions with a mass to charge ratio of $136.9\pm0.50$;
   b. determining the amount of the one or more ions by mass spectrometry; and
   c. using the amount of the one or more ions to determine the amount of said one or more analytes in the sample.

2. The method of claim 1, wherein the analytes are purified by immobilized boronic acid extraction prior to ionization.

3. The method of claim 1, wherein the analytes are purified by high performance liquid chromatography (HPLC) prior to ionization.

4. The method of claim 1, wherein said mass spectrometry is tandem mass spectrometry.

5. The method of claim 1, wherein one of the one or more analytes is epinephrine.

6. The method of claim 5, wherein said ionization further comprises generating ions with a mass to charge ratio of $107.0\pm0.50$.

7. The method of claim 6, wherein said ion with a mass to charge ratio of $166.1\pm0.50$ is a precursor ion that is fragmented by tandem mass spectrometry to provide a fragment ion with a mass to charge ratio of $107.0\pm0.50$.

8. The method of claim 1, wherein one of the one or more analytes is norepinephrine.

9. The method of claim 8, wherein said ionization further comprises generating ions with a mass to charge ratio of $107.0\pm0.50$.

10. The method of claim 9, wherein said ion with a mass to charge ratio of $151.9\pm0.50$ is a precursor ion that is fragmented by tandem mass spectrometry to provide a fragment ion with a mass to charge ratio of $107.0\pm0.50$.

11. The method of claim 1, wherein one of the one or more analytes is dopamine.

12. The method of claim 11, wherein said ionization further comprises generating ions with a mass to charge ratio of $91.0\pm0.50$.

13. The method of claim 12, wherein said ion with a mass to charge ratio of $136.9\pm0.50$ is a precursor ion that is fragmented by tandem mass spectrometry to provide a fragment ion with a mass to charge ratio of $91.0\pm0.50$.

14. The method of claim 1, wherein the amounts of two or more of the analytes from the group consisting of epinephrine, norepinephrine, and dopamine are determined in the same sample injection.

15. The method of claim 1, wherein the amounts of epinephrine, norepinephrine, and dopamine are determined in the same sample injection.

* * * * *